United States Patent

Cuny et al.

[11] 4,223,143
[45] Sep. 16, 1980

[54] QUINAZOLINE DERIVATIVES

[75] Inventors: Eckehard K. T. Cuny, Seeheim; Frieder W. Lichtenthaler, Mühltal, both of Fed. Rep. of Germany

[73] Assignee: Siegfried Aktiengesellschaft, Zofingen, Switzerland

[21] Appl. No.: 968,577

[22] Filed: Dec. 11, 1978

[51] Int. Cl.² .......................................... C07D 487/04
[52] U.S. Cl. ................................... 544/251; 544/287; 548/371
[58] Field of Search ........................................ 544/251

[56] References Cited
U.S. PATENT DOCUMENTS 3,624,205  11/1971  Hitchings et al. ................... 424/251

*Primary Examiner*—Paul M. Coughlan, Jr.
*Attorney, Agent, or Firm*—Werner W. Kleeman

[57] ABSTRACT

Novel quinazoline derivatives of the formula (1)

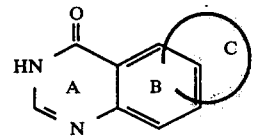

(1)

wherein ring C is a pyrazole ring fused to ring B in two vicinal positions thereof that are not fused with ring A. The novel formula (1) compounds or pyrazolo-quinazoline-ones are structurally related to allopurinol, a well known drug useful in the treatment of gout and are expected to replace or complement allopurinol in the therapeutic use thereof. The generic name Benzoallopurinol is suggested for the novel formula (1) compounds; formula (1) includes angular and linear structures of the interfused rings A, B and C.

Two methods for producing the novel formula (1) compounds are disclosed. The first method starts from the indazole structure that includes the interfused rings B and C, and ring A is formed on the indazole moiety. The second method starts from the quinazoline structure that includes interfused rings A and B, and the pyrazole ring C is formed on the benzo moiety (ring B) of the quinazoline structure. Either method may lead to angular or linear benzoallopurinols depending upon the substituents introduced into the starting structure for forming the complemental ring thereon.

7 Claims, No Drawings

QUINAZOLINE DERIVATIVES

BACKGROUND OF THE INVENTION

1. Field of the Invention

The present invention relates to novel quinazoline derivatives and more particularly to such quinazolinone derivatives having a pyrazole ring fused to the benzo moiety of the quinazolinone.

2Description of the Prior Art

Pyrazolo [3,4-d]-pyrimidine-4-one having the formula

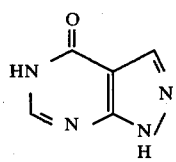

is well known under the generic name Allopurinol. Since its first preparation more than two decades ago (cf. R. K. Robbins, J. Am. Chem. Soc. 78, 1956, 784) it has been used for therapeutical purposes as an inhibitor of xanthine oxidase and for its controlling effect upon the concentration of uric acid in human blood; it is probably the most widely used drug for the treatment of gout and similar metabolic diseases of the human body. Because of the relatively low solubility of allopurinol and the need to use it at a relatively high dosage level, there is a substantial need to find new compounds that have a sufficient structural similarity with allopurinol to retain or increase its beneficial effects and/or to provide such allopurinol-related substances that have generally more favorable physiological and therapeutic effects than allopurinol.

Accordingly, it is a main object of this invention to provide for novel compounds that include the effective moieties of allopurinol in a modified structural arrangement.

Another object is a method of producing novel compounds that include the allopurinol moieties.

A further object is to provide for allopurinol-related compounds for therapeutic use instead of, or in combination with, allopurinol.

Other objects will become apparent as the specification proceeds.

SUMMARY OF THE INVENTION

According to the present invention we have found a group of novel compounds of the formula (1)

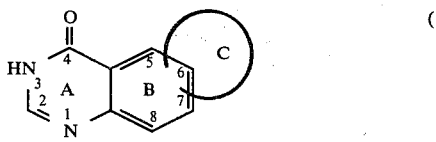

wherein ring C is a pyrazole ring fused to ring B—the benzo moiety—of said formula (1) in two vicinal positions of ring B selected from the group consisting of vicinal positions 5/6, 6/7 and 7/8 of ring B, i.e. those carbon atoms of ring B that are not involved in the fusion of ring B with ring A.

It will be understood that the novel formula (1) compounds might have either the 4-keto structure as shown or the corresponding enole structure

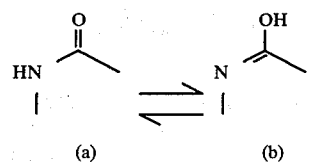

as has been ascribed in allopurinol. Also, the position of the hydrogen atom connected with one nitrogen atom of the pyrazole moiety might change between the structure

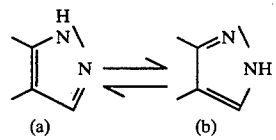

While present evidence seems to indicate predominance of the 4-keto structure (a) over the 4-enole structure (b) and predominance of the pyrazolo structure (a) over (b), the invention is to encompass either variation. The generic name "benzoallopurinol" is suggested for the novel formula (1) compounds.

According to a first general method according to the invention the novel formula (1) compounds can be obtained either:

(I) by providing a corresponding indazole precursor compound (i.e. one having rings B and C) that has suitable substituents on ring B in the selected vicinal positions and forming ring A fused to ring B; this synthesis will be referred to herein as the "indazole route"; or (II) by providing a corresponding quinazoline-4-one precursor compound (i.e. one having rings A and B) that has suitable substituents on ring B in the selected vicinal positions and forming ring C fused to ring B; this synthesis will be referred to herein as the "quinazoline route".

GENERAL DISCUSSION OF PREFERRED EMBODIMENTS

As will be apparent from the above, the novel formula (1) compounds or benzoallopurinols may have an "angular" structure, e.g.

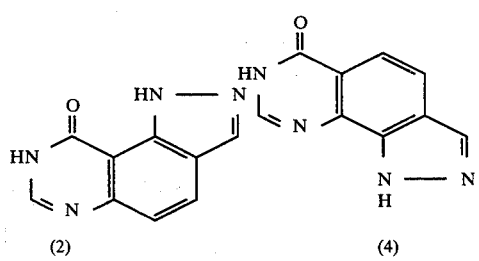

or a linear structure, e.g.

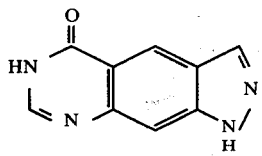

The "proximal" angular structure (formula 2) is particularly preferred, as is the linear structure (formula 3).

It is to be noted that the linear structure can be obtained via the indazole route, whereas both of the angular structures are accessible via the indazole approach and the quinazoline route, selection of either route being a question of convenience rather than principle.

Cyclization methods suitable for either route are known per se, but neither starting material, i.e. o-aminoindazolcarboxylic acid derivatives of type (1a) nor o-aminoquinazolinonecarboxylic acid derivatives of type (1b) have so far been accessible.

Preferably, when using the indazole route for synthesis of the formula (1) compounds, an indazole compound or precursor of the formula (1a)

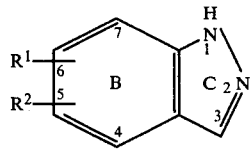

is employed, in which the substituents $R^1$, $R^2$ are in 5/4, 5/6 or 6/7 position of ring B. A preferred $R^1$ is the cyano group or the group

wherein X is lower ($C_1$–$C_4$) alkoxy, amino or halogen; X could stand for hydroxy or the like but this is less preferred. A preferred $R^2$ in formula (1a) is amino but could be substituted or protected (e.g. acylated amino) amino. Further, the hydrogen at N-1 or N-2 of ring C in formula (1a) could be substituted, e.g. by lower alkyl or by acyl or another group for protecting and/or modifying the pyrazole moiety.

When starting from the formula (1a) indazole precursor and using the preferred $R^1$, $R^2$ substituents in vicinal positions of ring B, ring closure or cyclization for forming ring A can be effected by reaction with formamide (preferred), N-alkylformamide, urea, formic acid, etc., or mixture of such reactants, generally at elevated temperatures, e.g. from 100 to 200° C.

When operating by the quinazoline route for preparing the novel formula (1) compounds, a suitable precursor is a quinazoline-4-one of the formula (1b)

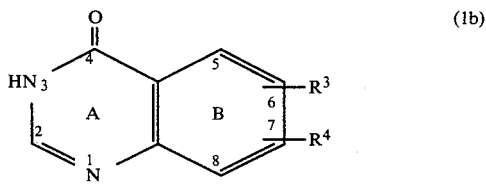

in which the substituents $R^3$, $R^4$ are vicinal as explained above. A preferred example of $R^3$ is $-N_2^{\oplus}Y^{\ominus}$ wherein $Y^{\ominus}$ is an anion, e.g. $BF_4^{\ominus}$. A preferred example of $R^4$ is methyl but could be another $C_1$ group.

When starting from the formula (1b) precursor and using the above mentioned preferred $R^3$, $R^4$ substituents, the desired cyclization for forming ring C can be effected advantageously in the presence of a reaction adjuvant, such as pyridine or a similar organic base, e.g. tetramethyl ammonium acetate, and the like at room temperature or slightly elevated temperatures of up to 100° C.

The preparation of the compound of formula (2) by either the indazole route or the quinazoline route will be explained, by way of example, on the basis of the following reaction scheme:

Reaction Scheme I

Indazole Route:

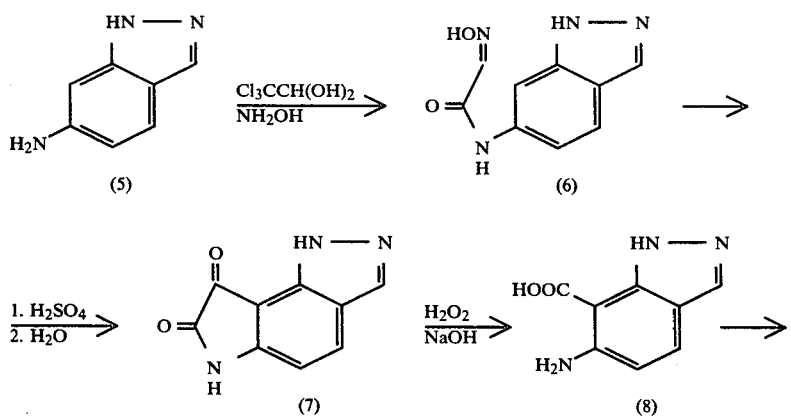

Reaction Scheme I -continued

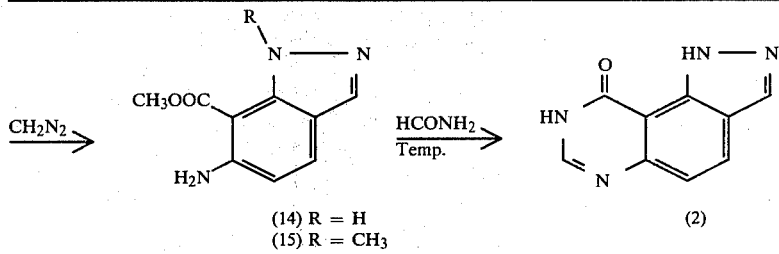

Quinazoline Route:

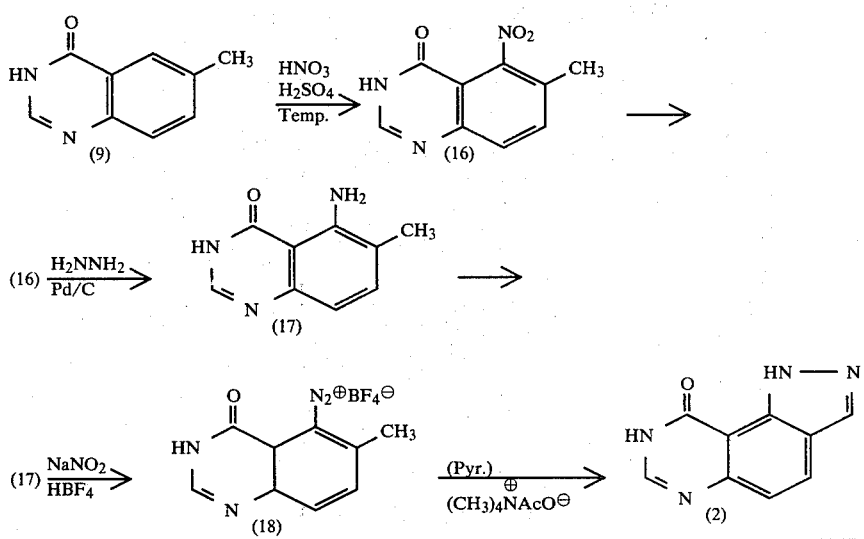

(Ac = acetyl)

With reference to the indazole route of scheme I above: preparation of the novel isatine compound (7) was effected by reacting the 6-amino indazole (5) with chloral hydrate and hydroxyl amine hydrochloride to procedure the 6-(α-oximinoacetyl)-amino-indazole (6) that is precipitated as a crystalline substance by salting out, e.g. with sodium sulfate and can be condensed without purification by means of sulfuric acid to yield pyrazolo-isatins, such as the 1,6,7,8-tetra-hydropyrrolo [2,3-g]-indazole-7,8-dione of the formula (7). Due to the preferred electrophillic attack of the oximino group in C-7 and not the other possible C-5 a pronounced regio-selectivity is achieved; this is apparent from NMR analysis showing two 8.5 Hz doublet signals of the aromatic protons H-4 and H-5. Subsequent oxidation of (7), e.g. by means of hydrogen peroxide in an aqueous alkali hydroxide yields the 6-aminoindazole-7-carboxylic acid (8) having no sharp melting point as is typical for anthranilic acids and amino acids and cannot be recovered in sufficient purity for elemental analysis by repeated recrystallization from methanol.

Esterification of acid (8) under mild reaction conditions, e.g. with diazomethane under cooling, yields the expected O-alkylation and some N-alkylation, i.e. produces a 10:1 (by weight mixture of the formula (14), the methyl ester of 6-aminoindazole-7-carboxylic acid and the N-alkylated homologue, i.e. the methyl ester of 6-amino-1-methylindazole-7-carboxylic acid (formula 15, not shown in the above diagram). The desired formula (14) compound can be isolated from the mixture by fractionated crystallization. Conventional acid-catalyzed esterification of (8) with methanol tends to decarboxylate the latter yielding the starting product (5).

The formula (14) ester can be smoothly reacted according to a Niementowski reaction (c.f. the above German Sandmeyer Patent No. 113,848 and J. F. Meyer et al, J. Org. Chem. 8, 1943, 239) with formamide at melt-producing temperatures to yield the target compound (2). On the other hand, a direct cyclization of the free acid (8) with formamide tends to cause decarboxylation of (8) even under relatively mild conditions (120° C. in an inert solvent, such as "Cellosolve").

With reference to the quinazoline route of the above reaction scheme I: the starting compounds (9) can be obtained easily by a Niementowski reaction from 2-amino-5-methylbenzoic acid. A preferred modification of preparing compound (9) will be explained below in Example VI and provides for a product (9) of higher purity and increased yields.

Subsequent nitration with nitration acids of different strength yields only the desired formula (16) compound. This surprising regio-selectivity in view of the electrophillic aromatic substitution can be explained by a directing effect of the pyrimidine ring. The influence of the methyl group is not significant because no 6-methyl-7-nitroquinazoline-4-one can be detected by chromatographic methods in the crude reaction product. The position of the nitro group of compound (16) was verified by NMR analysis.

Compound (16) is hydrogenated, e.g. by means of a palladium-on-charcoal and hydrazine to yield the 5- amino-6-methylquinazoline (17), the structure of which was ascertained by NMR analysis and derivatization with acetic anhydride in pyridine or in acetic acid.

Because of the thermal instability of diazonium salts and their tendency to explode, the amine (17) was not diazotized in hydrochloric acid solution but rather in the presence of fluoroborohydric acid. When using the hydrochloride of compound (17), a less satisfactory result was obtained, while dissolving of the free amine (17) in acetic acetate provides for a substantially quantitative conversion of (17).

The 6-methylquinazoline-4-one-5-diazonium tetrafluoroborate (18) thus formed precipitates in a crystalline form, has a high thermal stability (decomposition only at temperatures above 157° C.) and can be stored without problems for periods of several months at room temperature. Thus, compound (18) is a particularly preferred precursor compound for the inventive process.

The cyclization of the precursor (18) to form the pyrazolo moiety (ring C of formula 1) fused on the benzo moiety in this synthesis route can be effected, for example, in the presence of a weak base, such as pyridine or tetramethylammonium acetate. This tends to promote the intramolecular coupling with elaboration of the pyrazole ring of the indazole structure the nucleophilicity of the methyl group being enhanced by the vicinal diazo moiety.

Another varient of this procedure would be based upon the N-nitrosation of 5-acetamido-6-methylquinazoline-5-one (the N-acetyl derivative of the above compound 17) at the acetamido group but this is a less preferred approach because of the well known toxicity of nitroso amines.

Spectroscopic and physical data of the formula (2) compounds obtained by both the indazole route and the quinazoline route confirm the identity of the products of each route.

The above reaction scheme I is given to illustrate preferred methods of producing angular benzoallopurinols according to the invention. The linear benzoallopurinol of formula (3) is particularly preferred since its molecular geometry—as compared to that of the conventional allopurinol—is lengthened but in one direction by about 2.4 Å, whilst in the angular benzoallopurinols (2) and (4) the pyrimidine and pyrazole structural features of the allopurinol are extended via a kink, i.e. in a somewhat more complex manner.

In both the angular and the linear benzoallopurinols according to the invention, and particularly in the case of the preferred benzoallopurinol (3), the insertion of the benzene ring into the conventional allopurinol structure retains the enzyme-bonding sites of the terminal rings and increases the potential for $\pi$-interactions.

The following reaction scheme II illustrates a synthesis of the linear benzoallopurinol according to the invention.

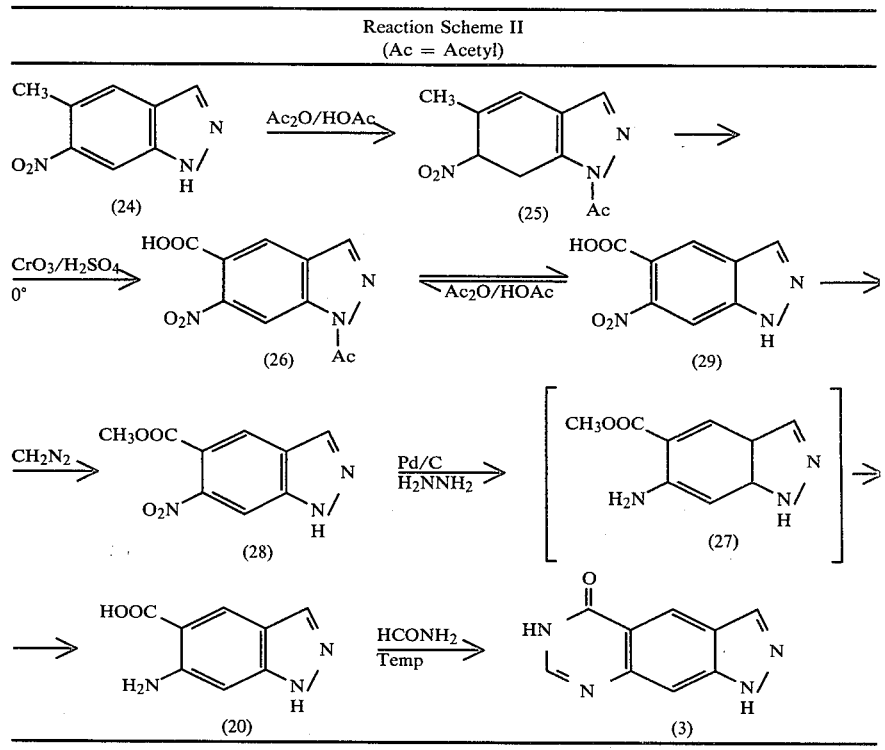

While other methods for forming the target compound (3) of reaction scheme II are feasible, the illustrated synthesis via the indazole route is preferred because of the easy availability of the starting substance and the possibility to form the carboxyl group in 5-position of the indazole structure advantageously by oxidation of a side chain.

Starting from the known compound of formula (24), the 5-methyl-6-nitroindazole, this compound is reacted to first protect the 1-nitrogen atom, e.g. by reacting it with the anhydride of an organic acid, preferably acetic anhydride, using a diluent, such as acetic acid, pyridine or the like. NMR analysis (sharp acetyl resonance) shows that this reaction is quite selective.

The acetylated compound of formula (25) thus obtained is oxidized for transforming the 5-methyl into 5-carboxyl, e.g. by conventional side-chain oxidation methods such as reaction with chromic trioxide ($CrO_3$) and sulfuric acid at low temperatures (e.g. about 0° C.). The compound obtained is 6-nitroindazole-5-carboxylic acid (formula 29) and is relatively unstable as it tends to decarboxylate. Thus, the acid (29) or its immediate precursor (formula 26) preferably is not isolated but rather esterified directly, e.g. with diazomethane, to yield the corresponding ester, preferably the methyl ester of the 5-carboxy acid. To avoid an undesirable bis-alkylation or bis-methylation, respectively (i.e. not only O-alkylation but N-alkylation as well), such esterification is preferably effected at low temperatures (e.g. in the order of 0° C.) as this tends to suppress bis-alkylation.

While the overall yield over the four steps from (24) through (25) to (28) has been found to be somewhat low, (e.g. in the order of 10%, the intermediate product (28) of this route is obtained in the form of crystals of analytic puritiy and its production can be effected easily under commercial manufacturing conditions. The structure of the novel formula (28) intermediate has been ascertained by NMR analysis and this novel and preferred compound according to the invention may also be used for syntheses other than benzoallopurinol production.

The 1-acetyl intermediate of formula (26) will be deacetylated to (29) under the acid oxidation conditions, yet can readily be obtained by reacetylation of (29).

Reduction of the nitro ester of formula (28) under conditions to convert the 6-nitro group into the 6-amino group, e.g. by means of a hydrogenating agent such as hydrazine and, if required, in the presence of a hydrogenation catalyst such as a metal from group VIII of the periodic system of elements (e.g. Pt, Pd, etc.) on a suitable catalyst support such as charcoal, yields the 6-aminoindazole-5-carboxylic acid of formula (20). Upon such reduction, the ester, e.g. the methyl ester, of the 6-aminoindazole-5-carboxylic acid is formed first (formula 27) and could be isolated. However, hydrogenation—notably under alkaline conditions (hydrazine)—will lead to hydrolysis of the ester as well so that the acid (20) will be obtained "directly" as a result of hydrogenating compoun (28). So, while the conversion of (28)→(20) involves two reactions and could be carried out in two distinct steps, both reactions are preferably combined into a reduction/hydrolysis operation.

The final cyclization step could be carried out with the ester (27) or its 5-carboxamido analog but is preferably performed with the free amino acid (20), which has a thermal stability that is sufficient to permit cyclization, e.g. with formamide, at elevated temperatures (100°–200° C.) in satisfactory yields, e.g. 30–40%, the direct or combined conversion of (28)→(20) being preferred embodiment.

The final step of reaction scheme II thus is cyclization to form ring A of the formula (1) target compound, specifically the pyrimidine ring of the linear benzoallopurinol (3).

The above reaction sequences are presented for illustration and not for limitation as both the formation of the pyrimidine ring (ring A) and of the pyrazole ring (ring C) fused to a benzo moiety could be effected by other methods than those set forth above.

Further, it will be apparent to those experienced in the art that specific substituents mentioned above for illustration, e.g. the specific alkyls in the ester groups of compounds (14), (27), (28) may be modified as such alkyls do not appear in the formula (1) target products and other alkyls, preferably lower or $C_q$—$C_4$ alkyls or equivalent groups could be used instead of methyl. By the same token, the acetyl of formulae (25) and (26) could be replaced by other acyl groups and, again, the specific selection is believed to be one of convenience rather then principle. This would apply quite generally to the various reaction media, reactants and reaction conditions mentioned above as long as the target compounds of formula (1) will be formed by the syntheses disclosed and no undue experimentation is required to decide what alternatives are suitable for the purposes of the invention.

Specific Examples embodying the invention are set forth below. These Examples are illustrative and not to be understood as limiting the scope and underlying principles of the invention in any way. In the Examples, temperatures are in degree (°) Centigrade, percentages are by weight. Melting points (m.p.) were determined on a Bock Monoskop and are uncorrected. NMR, IR and mass spectra were taken to ascertain the structures. Results of elemental analysis are in precent by weight. The NMR spectra were obtained on a "Varian A60" and "XL-100°" spectrometer using TMS (tetramethylsilane) as an internal standard; chemical shifts are expressed as parts per Million ($\delta$) from TMS. IR spectra were determined in pressed disks of potassium bromide using a "Beckman 125" spectrophotometer. The mass spectra were obtained on a "Varian CH 34" and "MAT 311A" spectrometer. Thin layer chromatography was run on silicagel/plastic plates ("Kieselgel $F_{254}$") and column chromatography was done on silicagel ("Kieselgel 60", Merck, Darmstadt, West-Germany).

EXAMPLE I 6-($\alpha$-Oximinoacetyl)-amino-1H-indazole (formula 6)

6-Amino-1-H-indazole (formula 5) (13.3 g, 0.1 mol) was dissolved in a mixture of water (60 ml) and concentrated hydrochloric acid (10 ml, 0.1 mol). The solution was contacted with a mixture of aqueous chloral hydrate (16.5 g, 0.1 mol in 250 ml water), sodium sulfate hydrate (260 g) and aqueous hydroxylamine hydrogen chloride (22.0 g, 0.3 mol in 100 ml water) under reflux conditions for a period of 1 to 2 min. The product that formed on cooling was collected, washed and dried ($CaCl_2$); 16.1 g (79%) of the formula 6 compound were obtained as a brown powder, m.p. 199°–201°; ir (KBr): 1520, 1560, 1590, 1642, 1685 cm$^{-1}$ (aromatic, amide, >C=N—OH); pmr (100 MHz, DMSO-d$_6$); $\delta$ 7.00–9.20 ($D_2O$-exchangeable broad m, 3.2, OH, NH, 1.2 HCl); 7.30 (d, 1, J=9 Hz, H4), 7.73 (d, 1, J=9 Hz, H5), 7.78 (s, 1, H7), 8.07 and 8.26 (2s, 2, H3, H3'), 10.28 (s, 1, $D_2O$-exchangeable, NH-1); ms (70 eV): m/e 204 (18%, M$^+$), 187 (24%, M$^+$—OH), 159 (100%, M—$H_2O$ and HCN).

Anal. calc. for $C_9H_8N_4O_2 \cdot 1.25HCl$ (249.8): C 43.27, H 3.73, N 22.43. found: C 43.69, H 3.66, N 21.94.

The above mentioned starting compound (formula 5) can be obtained by the method of R. R. Davis, J. Chem. Soc., 1955, page 2412.

EXAMPLE II 1,6,7,8-Tetrahydro-pyrrolo[2.3-g]-indazole-7,8-dione (formula 7)

37.3 g (0.18 mol) of 3'-oximino-6-acetamido-1H-indazole (formula 6, product of Example I) were added gradually to 65 ml of concentrated sulfuric acid while stirring at 50°. The solution obtained was heated to 80° for a period of 10 min. On treatment with 350 g of ice for a period of 30 min, the cooled solution formed a residue which was collected and washed with cold water, dissolved in 180 ml of water with addition of a 40% slution of sodium hydroxide, and treated with 2 N hydrochloric acid until precipitation occurred. The residue was filtered off and the filtrate was brought to a pH of 4 to 5 by addition of concentrated hydrochloric acid. The solution was allowed to stand at room temperature for 30 min and the product formed thereby was collected, washed with water and dried ($CaCl_2$) under vacuum; 31.5 g (85%) of the monohydrate of the formula 7 compound were obtained as a wine-red powder, m.p. >300°; recrystallization from water followed by drying under vacuum ($P_2O_5$) at 80°–90° yielded wine-red stocky crystals of the formula 7 compound, m.p. >300°; ir (KBr): 1600, 1640, 1650 (aromatic), 1725, 1750 $cm^{+1}$ (>C=O, γ-lactam); pmr (DMSO-$d_6$): δ ca. 6.50 ($D_2O$-exchangeable broad m, 3, NH6, C(OH)$_2$ 7), 6.77 (d, 1, J=8.5 Hz, H4), 8.11 (s, 1, H3), 8.13 (d, 1, J=8.5 Hz, H5), 11.07 (s, 1, NH1 not exchangeable with $D_2O$ due to strong hydrogen bonding); ms (70 eV): m/e 187 (65%, M+), 159 (100%, M+—CO), 131 (61%, M+—2CO), 104 (65%, M+—2CO—HCN), 77 (40%, M+—2CO—2HCN).

Anal. calc. for $C_9H_5N_3O_2$ (187.2): C 57.76, H 2.69, N 22.45. found: C 57.14, H 2.67, N 22.28.

EXAMPLE III

6-Amino-1H-indazole-7-carboxylic acid (formula 8)

1,6,7,8-Tetrahydro-pyrolo[2.3-g]-indazole-7,8-dione (formula 7, product of Example II) (9.4 g, 50 m-mol) was dissolved in aqueous sodium hydroxide (10%, 100 ml) followed by the addition of 10% aqueous hydrogen peroxide (17 ml, 50 m-mol) at 100°. The mixture was kept at 100° for 10 min whereafter $CO_2$ formation ceased, and subsequently brought to pH 4.0 to 5.5 by the addition of conc. hydrochloric acid. The resulting compound (formula 8) was collected, washed with cold water and dried ($CaCl_2$) in vacuum to yield 7.71 g (87%) of the target compound as a brown powder, m.p. from 177° on (dec.); ir (KBr): 1580, 1630, 1660 $cm^{-1}$ (aromatic, acid-CO); pmr (100 Hz, DMSO-$d_6$) δ 6.70 (d, 1, J=9 Hz, H4), ca. 6.80–9.00 ($D_2O$-exchangeable broad m, 2, $NH_2$), 7.66 (d, 1, J=9 Hz, H5), 7.93 (s, 1, H3); ms (70 eV): m/e 177 (100%, M+), 159 (86%, M+—$H_2O$). A sample recrystallized from methanol failed to give significant data by elemental analysis.

EXAMPLE IV

Methyl ester of 6l -amino-1H-indazole-7-carboxylic acid (formula 14) and methyl ester of 6-amino-1-methyl-1H-indazole-7-carboxylic acid (formula 15)

A solution of diazomethane in diethyl ether was added carefully to an ice-cooled stirred solution of 6-amino-1H-indazole-7carboxylic acid (formula 8, product of Example III) (530 mg, 3 m-mol) in aqueous methanol (10%, 30 ml). The mixture was kept at room temperature for 30 min. Then, it is evaporated in vacuum and the residue obtained was dissolved in chloroform (50 ml); the solution was successively washed with aqueous sodium hydroxide (2 N, 2×20 ml) and water (20 ml). Upon drying of the solution ($Na_2SO_4$) and evaporation of the dry solution in vacuum 0.474 g of an orange-red crystalline mixture of formulae 14 and 15 compounds were obtained. The mixture was dissolved in diethyl ether (30 ml) and concentrated in vacuum to a volume of 10 ml. Light yellow crystals of the formula 14 compound (260 mg, 45%) were obtained. Further quantities of the formula 14 compound could be obtained by evaporation of the mother liquor to dryness in vacuum, elution of the residue from a silica gel column with 4:3:1 ethyl acetate-water-n-propanol and evaporation of the major fraction. The total yield of formula 14 compound was 64%, m.p. 179°–181°; ir (KBr): 1587, 1633, 1675 $cm^{-1}$ (atomatic, ester CO); pmr (100 MHz, DMSO-$d_6$): δ 4.00 (s, 3, $CH_3OCO$), 7.36 (d, 1, $J_{4,5}$=9 Hz, H4), 7.36 ($D_2O$-exchangeable s, 2, $NH_2$), 7.69 (d, 1, $J_{4,5}$=9 Hz, H5), 7.94 (s, 1, H3), 12.55 ($D_2O$-exchangeable s, 1, NH): ms (70 eV): m/e 191 (100%, M+), 159 (98%, M+—$CH_3OH$), 131 (32%, M+—$CH_3OH$—CO).

Anal. calc. for $C_9H_9N_3O_2$ (191.2): C 56.54, H 4.75, N 21.98. found: C 57.05, H 4.80, N 21.70.

The minor fraction from the above column separation was evaporated to dryness and yielded the formula 15 compound (40 mg, yield =6%); m.p. 218°–219°; ir (KBr): 1595, 1622, 1667 $cm^{-1}$ (aromatic, ester-CO); pmr (100 MHz, DMSO-$d_6$): δ 3.84 and 4.05 (2s, 3 each, $CH_3OCO$, $CH_3N$), 6.64 (d, 1, $J_{4,5}$=9 Hz, H4), 7.36 ($D_2O$-exchangeable s, 2, $NH_2$), 7.60 (d, 1, $J_{4,5}$=9 Hz, H5), 8.12 (s, 1, H3); ms (70 eV): m/e 205 (28%, M+), 173 (29%, M+—$CH_3OH$), 245 (8%, M+—$CH_3OH$—CO).

Anal. calc. for $C_{10}H_{11}N_3O_2$ (205.2): C 58.53, H 5.40, N 20.48. Found: C 57.86, H 5.43, N 19.75.

EXAMPLE V

1H-Pyrazolo[3,4-f]-quinazoline-9-one (prox-Benzoallopurinol) (formula 2)

6-Amino-1H-indazole-7-carboxylic acid methyl ester (formula 14, obtained according to Example IV) (1.35 g, 7.0 m-mol) was heated with formamide (4.2 ml) at 140° for a period of 4 hours and again at 180° for a period of 1.5 hours. The product that formed on cooling was collected and washed with a small amount of cold water to yield 555 mg of the formula 2 target compound. Additional amounts of the target compound were obtained by working-up the mother liquor. The cumulative product yield was 965 mg (74%), m.p. 325°–327° (decomp.); ir (KBr): 1570, 1620, 1685 $cm^{-1}$ (aromatic, C=C, C=N, CO); pmr (DMSO-$d_6$): δ 7.45 and 8.22 (2 d, 2, J=9 Hz, H4 and H5), 8.30 and 8.32 (2s, 2, H3 and H7), 13.44 (broad m, 2, $D_2O$-exchangeable $N^1$—H and $N^8$—H); ms (70 eV): m/e 186 (100%, M+), 158 (16%, M+—CO).

Anal. calc. for $C_9H_6N_4O$ (186.2): C 58.06, H 3.25, N 30.10. Found: C 57.98, H 3.20, N 30.02.

EXAMPLE VI

6-Methyl-5-nitro-quinazoline-4-one (formula 16)

6-Methylquinazoline-4-one (formula 9) (40.0 g, 0.3 mol) was gradually added to a mixture of fuming nitric acid (80 ml) and concentrated sulfuric acid (80 ml) kept at 18°. The mixture was stirred at room temperature for 30 min. The clear dark brown solution obtained by heating the mixture on a boiling water bath and by subsequent cooling was treated with crushed ice (1.2 kg). The resulting product was collected, washed with water (800 ml) and recrystallized from acetic acid (900 ml) to yield 35.0 g (67%) of the target compound 16, m.p. 304°–305° C.; ir (KBr): 1540 $cm^{-1}$ ($NO_2$); pmr (DMSO-d$_6$): δ 2.32 (s, 3, CH$_3$), 7.76 and 7.94 (2d, J=9 Hz, 2, H7, H8), 8.22 (s, 1, H2), 12.58 (broad m, 1, D$_2$O-exchangeable NH); ms (70 eV): m/e 205 (100%, M+).

Anal. calc. for C$_9$H$_7$N$_3$O$_2$ (205.2): C 52.68, H 3.44, N 20.48. Found: C 52.36, H 3.32, N 20.76.

The starting compound (formula 9) of this Example is known and can be prepared, for example, according to Niementowski, J. Prakt. Chemie, Volume 51 (1895), page 564, from 2-amino-5-methyl benzoic acid, using the modifications of the preparation disclosed by V. Oakes et al., J. Chem. Soc., 1962, 4678, and recrystallization from ethanol, to give a product of m.p. 261° (dec) in 73% yield.

EXAMPLE VII

5-Amino-6-methylquinazoline-4-one (formula 17)

An aqueous hydrazine solution (83%, 10 ml) in ethanol (10 ml) was added carefully at 28° under a nitrogen atmosphere to a mixture of 6-methyl-5-nitroquinazoline-4-one (formula 16, prepared according to Example VI) (10.0 g, 490 m-mol) and palladium-one-charcoal (10%, 1.0 g) in ethanol (150 ml). The mixture was refluxed for 1 hour. Cooling of the mixture to room temperature yielded crystals which were dissolved in dimethyl formamide (150 ml) and separated from the catalyst by filtration. The filtrate was evaporated and the residue recrystallized from ethanol. This yielded 7.0 g (82%) of the formula 17 target compound in the form of light yellow crystals, m.p. 260°-261° (decomp.); ir (KBr): 3480, 3315 cm$^{-1}$ (NH$_2$); pmr (DMSO-d$_6$): δ 2.13 (s, 3 CH$_3$), 6.70 (d, 1, J=8.5 Hz, H7), 6.95 (m, 2, D$_2$O-exchangeable NH$_2$), 7.36 (d, 1, J=8.5 Hz, H8), 7.88 (s, 1, H2), 11.67 (m, 1, D$_2$O-exchangeable NH); ms (70 eV): m/e 175 (100%, M+).

Anal. calc. for C$_9$H$_9$N$_3$O (175.2): C 61.70, H 5.18, N 23.99. Found: C 61.55, H 5.13, N 23.46.

EXAMPLE VIII

6-Methylquinazoline-4-one-5-diazonium-tetrafluoroborate (formula 18)

Aqueous tetrafluoroborohydric acid (35%, 5.04 g, 20 m-mol) was added to a suspension of 5-amino-6-methylquinazoline-4-one (formula 17, obtained according to Example VII) (1.75 g, 10 m-mol) in ethyl acetate (40 ml). The tetrafluoroborate of the formula 17 compound separated as a yellow residue which was dissolved by gradual addition of sodium nitrite (0.75 g, 10 m-mol) within 30 min under stirring at 5°. The solution was stirred for an additional period of 1 hour. Pale green crystals that formed at the iodide/starch end point were collected and washed well with ethyl acetate. This yielded 2.75 g (100%) of the formula 8 compound, m.p. 157° (decomp.). The crude product was purified by dissolving it in acetone and precipitation by addition of diethyl ether. ir (KBr): 2280 cm$^{-1}$ (—N$^⊕$=N, sharp); pmr (DMSO-d$_6$): several aromatic signals due to decompositions; ms (70 eV): m/e 178 (48%, M+ of 5-fluoro-6-methylquinazoline-4-one formed by Schiemann reaction during measurement); ms (FD): m/e 186 (100%, M+ of 5-diazo-6-methylquinazoline-4-one). No satisfactory elemental analysis could be obtained due to thermal lability of the product.

EXAMPLE IX prox-Benzoallopurinol (formula 2)

6-Methylquinazoline-4-one-5-diazonium-tetrafluoroborate (the formula 18 compound obtained according to Example VIII) (600 mg, 2,2 m-mol) was gradually dissolved in pyridine (20 ml) under cooling (tap water) and the solution was allowed to stand overnight at room temperature. The target formula 2 compound separated as a red-brown residue (205 mg). When the mother liquor was allowed to stand at room temperature and exposed to ambient air for several days, further portions of the formula 2 compound (280 mg) were obtained. The combined products were purified by elution from a silicagel column, first with 50:1 chloroform-methanol and, then, with 1:10 chloroform-methanol. The middle fraction of the latter eluant contained the formula 2 compound (168 mg, 44% yield, based on the formula 17 compound), m.p. 330° C. and is identical with the target (formula 2) compound of Example V. The first eluate contained 5-amino-6-methylquinazoline-4-one (29 mg, 7%), the last fraction gave some (20 mg, 5%) 5-azido-6-methylquinazoline-4-one (formula 19) as identified by their mass spectral data.

EXAMPLE X prox-Benzoallopurinol (formula 2)

6-Methylquinazoline-4-one-5-diazonium-tetrafluoroborate (formula 18), (695 mg, 2,5 m-mol), prepared from 5-amino-6-methylquinazoline-4-one (formula 17) (440 mg, 2,5 m-mol) as in Example VIII, was treated with a solution of tetramethyl ammonium acetate (1 g) in chloroform (25 ml) for 1 hour. The solution obtained was evaporated under vacuum. The residue formed was treated with ethanol (20 ml) to yield the formula 2 compound in the form of a yellow powder (80 mg), m.p. 325°. A portion of the crude formula 2 compound (85 mg) was purified as above to yield 26 mg (45%) of pure product, identical in all respects with the products of Example V and IX above.

EXAMPLE XI

1-Acetyl-5-methyl-6-nitro-indazole (formula 25)

(A) Five g (28,2 m-mol) of 5-methyl-6-nitro-1H-indazole (formula 24) prepared e.g. according to the method described by E. Nölting, Ber. Dtsch. Chem. Ges. 37 (1904) 2556 were added to a mixture of acetic acid (50 ml) and acetic anhydride (100 ml). After about 15 min the acetylated compound (formula 25) crystallized from the light-yellow colored solution in the form of elongated colorless needles. To complete crystallization, the solution was left to stand for a period of 45 min at room temperature and for a period of 15 hours in a refrigerator (4°). The crystal mass formed was filtered under suction, washed well with water and dried over P$_2$O$_5$ under vacuum. This yielded 4.6 g (yield 75%) of the formula 25 target product. By careful evaporation of the mother liquor and allowing to stand overnight in the refrigerator, an additional portion (0.90 g) of the target product was obtained. Total yield was 5.55 g (90%). The target product melts at 185°; ir (KBr): 1715 (ester carbonyl), 1582 (aromatic), 1530 cm$^{-1}$ (NO$_2$); pmr (CDCl$_3$): δ 2.66 (s, 3, C$^5$—CH$_3$), 2.82 (s, 3, N$^1$—CH$_3$CO), 7.70 (s, 1, H4), 8.18 (s, 1, H7), 8.96 (s, 1, H3); ms (70 eV): m/e 219 (35%, M+), 177 (61%, M+-keten), 160 (100%, M+-keten-HO).

Anal. calc. for C$_{10}$H$_9$N$_3$O$_3$ (219.2): C 54.79, H 4.14, N 20.48. Found: C 54.64, H 3.95, N 19.13.

(B) In an alternative procedure according to this Example XI, 500 mg (2.8 m-mol) of 5-methyl-6-nitro-1H-indazole (formula 24) were admixed with 10 ml of pyridine and 1 ml of acetic anhydride. The mixture was allowed to stand at room temperature for a period of 12 hours. The dark brown reaction solution was evaporated under vacuum and the residue obtained was post-evaporated twice with toluene (2×30 ml). Recrystallization from methanol (40 ml) yielded 230 mg (37%) of the crystalline compound (formula 25), m.p. 180°–182°. Upon evaporation of the mother liquor, 230 mg (46%) of the starting compound (formula 24) were recovered.

EXAMPLE XII

Methyl ester of 6-nitro-1H-indazole-5-carboxylic acid (formula 28)

Eleven g (50 m-mol) of 1-acetyl-5-methyl-6-nitro-indazole (formula 25, obtained according to Example XI) were suspended in 250 ml of concentrated sulfuric acid at +5°. Chromic trioxide (25 g) was added at this temperature within a period of 5 min in portions and the reaction mixture was stirred on an ice bath for additional 15 min. The temperature in the reaction flask rose briefly to 22° and some evolution of carbon dioxide was observed. Then, the reaction mixture was carefully poured onto about 1.8 liters of ice and extracted with diethyl ether (10×200 ml). The combined ether extracts were neutralized with solid sodium bicarbonate and evaporated under vacuum to a volume of about 300 ml. For methylation of the product obtained, 80 ml of a solution of diazomethane in diethyl ether was added at 0° while stirring during a period of 30 min. The reaction solution was filtered, evaporated under vacuum, and the residue was mixed with chloroform. This yielded 830 mg (7.5%) of target compound (formula 28) in the form of chromatographically uniform crystals, m.p. 162°; ir (KBr): 1535 ($NO_2$), 1545, 1625 (aromatic), 1750 $cm^{-1}$ (ester carbonyl); pmr (DMSO-$d_6$): δ 3.88 (s, 3, $CH_3OCO$), 8.30, 8.44, 8.46 (3s, 3, H3, H4, H7), 13.90 (broad m, 1, with $D_2O$ exchangeable, $N^1H$); ms (70 eV): m/e 221 (47%, $M^+$), 190 (100%, $M^+$—$CH_3O$).

Anal. calc. for $C_9H_7N_3O_4$ (221.2): C 48.87, H 3.19, N 19.00. Found: C 48.74, H 3.09, N 19.41.

EXAMPLE XIII

6-Amino-1H-indazole-5-carboxylic acid (formula 20)

A mixture of 250 mg (1.1 m-mol) of the methyl ester of 6-nitro-indazole-5-carboxylic acid (the compound of formula 28 obtained according to Example XII) and 100 mg palladium-on-carbon catalyst in ethanol (10 ml) was prepared and kept under gaseous nitrogen. A mixture of an 85% aqueous solution of hydrazine hydrate (1 ml) and ethanol (1 ml) was added dropwise within a period of 1 hour to the reaction mixture. The resulting mixture was stirred during a period of 1 hour at room temperature; then, an additional amount of the catalyst (100 mg) and of the hydrazine hydrate solution (1 ml) was added and the mixture kept under reflux for a period of 4 hours. After cooling to room temperature, the catalyst was removed by filtration and the remaining reddish-brown reaction solution was evaporated under vacuum. The residue obtained was post-evaporated with toluene (2×30 ml). The reddish-brown powder obtained was dissolved in methanol (20 ml), mixed with diethyl ether (30 ml) and allowed to stand overnight in the refrigerator. As a result, 135 mg (69%) of the product were obtained in form of light yellow crystals that start to sublimate at 260° to form needles melting at 283°; ir (KBr): 1640 (carbonic acid carbonyl), 1590 $cm^{-1}$ (aromatic); pmr (DMSO-$d_6$): δ 6.68, 7.95, 8.32 (3s, 3, H3, H4, H7), 7.2–9.0 (with $D_2O$ exchangeable, broad m, 4, $NH_2$, NH, COOH); ms (70 eV): m/e 177 (81%, $M^+$), 159 (100%, $M^+$—$H_2O$), 132 (97%, $M^+$—COOH).

The recrystallized sample failed to yield significant data upon elemental analysis.

EXAMPLE XIV

1H-Pyrazolo[4,5-g]-quinazoline-5-one (formula 3; lin-Benzoallopurinol)

450 mg (2.5 m-mol) of 6-amino-indazole-5-carboxylic acid (formula 20, prepared according to Example XIII) in 3 ml of formamide were heat-melted and kept at a temperature of 140° during a period of 4.5 hours and then at a temperature of 180° during another period of 1.5 hours. The mass obtained was cooled to room temperature. The product was filtered under suction, washed well with water until the filtrate became clear, and then washed with a small amount of ethanol. The target product (formula 3) was recovered in an amount of 167 mg (36%) in the form of a greyish-brown, finely crystalline material, m.p. 330°. The product was uniform as evidenced by chromatography; pmr (DMSO-$d_6$): δ 7.78, 8.10, 8.44, 8.76 (4 broad s, 4, H3, H4, H7, H9), 11.92, 13.36 (2 with $D_2O$ exchangeable broad m, 2, $N^1H$, $N^6H$), (DMSO-$d_6$/$D_2O$): δ 7.83, 8.10, 8.45, 8.78 (4 sharp s, 4, H3, H4, H7, H9); ms (70 eV): m/e 186 (100%, $M^+$).

Anal. calc. for $C_9H_6N_4O$ (186.2): C 58.06, H 3.25, N 30.10. Found: C 57.97, H 3.10, N 29.98.

Various modifications of the above disclosed specific embodiments of the invention will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. A compound of the formula (1)

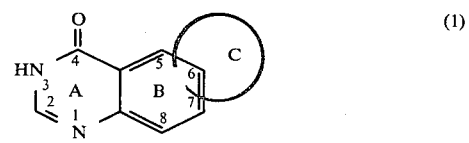

wherein ring C is a pyrazole ring fused to ring B of said formula (1) in two vicinal positions of ring B selected from the group consisting of vicinal positions 5/6, 6/7 and 7/8 of ring B.

2. The compound of claim 1 wherein said ring C is fused to said 5/6 vicinal positions of ring B.

3. The compound of claim 1 wherein said ring C is fused to said 6/7 vicinal positions of ring B.

4. The compound of claim 1 wherein said ring C is fused to said 7/8 vicinal positions of ring B.

5. The compound of claim 1 having the formula (2)

6. The compound of claim 1 having the formula (3)
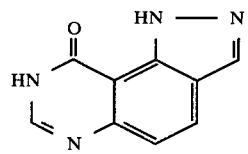
(2)
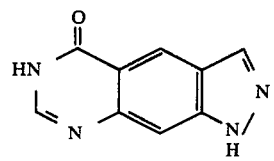
(3)
7. The compound of claim 1 having the formula (4)
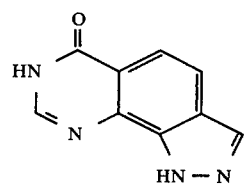
(4)
* * * * *